(12) United States Patent
Matsumura et al.

(10) Patent No.: US 9,034,843 B2
(45) Date of Patent: May 19, 2015

(54) OPHTHALMIC COMPOSITION

(75) Inventors: Yasuko Matsumura, Osaka (JP); Kazuhiro Fukushima, Osaka (JP)

(73) Assignee: Rohto Pharmaceutical Co., Ltd., Osaka-Shi (JP)

( * ) Notice: Subject to any disclaimer, the term of this patent is extended or adjusted under 35 U.S.C. 154(b) by 136 days.

(21) Appl. No.: 12/677,988

(22) PCT Filed: Sep. 11, 2008

(86) PCT No.: PCT/JP2008/066415
§ 371 (c)(1),
(2), (4) Date: Mar. 12, 2010

(87) PCT Pub. No.: WO2009/035033
PCT Pub. Date: Mar. 19, 2009

(65) Prior Publication Data
US 2010/0216741 A1    Aug. 26, 2010

(30) Foreign Application Priority Data

Sep. 14, 2007 (JP) .................................. 2007-239044
Feb. 8, 2008 (JP) .................................. 2008-028981

(51) Int. Cl.
| A61K 31/726 | (2006.01) |
| A61K 31/734 | (2006.01) |
| A61K 31/74 | (2006.01) |
| A61K 9/00 | (2006.01) |
| A61K 31/717 | (2006.01) |
| A61K 31/721 | (2006.01) |

(52) U.S. Cl.
CPC ............ *A61K 9/0048* (2013.01); *A61K 31/717* (2013.01); *A61K 31/721* (2013.01); *A61K 31/726* (2013.01); *A61K 31/734* (2013.01); *A61K 31/74* (2013.01); *Y10S 514/839* (2013.01)

(58) Field of Classification Search
CPC .............................. A61K 9/0048; A61F 9/0061
USPC ...................... 514/839, 57, 54, 59, 772.2, 781
See application file for complete search history.

(56) References Cited

U.S. PATENT DOCUMENTS

| 5,185,372 | A | * | 2/1993 | Ushio et al. .................... 514/552 |
| 6,511,949 | B1 | * | 1/2003 | Nitta et al. ..................... 510/112 |
| 8,067,038 | B2 | * | 11/2011 | Arita et al. ..................... 424/725 |
| 2010/0011989 | A1 | * | 1/2010 | Arita et al. .................. 106/217.8 |

FOREIGN PATENT DOCUMENTS

| JP | 2001-247466 A | 9/2001 |
| JP | 2005-172912 A | 6/2005 |
| JP | 2005-187345 A | 7/2005 |
| JP | 2005-343893 A | 12/2005 |
| JP | 2006-22087 A | 1/2006 |
| JP | 2006-52160 A | 2/2006 |
| JP | 2006-143590 A | 6/2006 |
| JP | 2006-193521 A | 7/2006 |
| JP | 2006-219484 A | 8/2006 |
| JP | 2006-282586 A | 10/2006 |
| JP | 2007-77053 A | 3/2007 |
| WO | WO 2006/105183 A1 | 10/2006 |
| WO | WO 2007/088783 A1 | 8/2007 |
| WO | WO 2007/145344 A1 | 12/2007 |

OTHER PUBLICATIONS

English Translation of International Preliminary Report on Patentability (PCT/IB/373) and Written Opinion of the International Searching Authority (PCT/ISA/237) for Intl. Apln. No. PCT/JP2008/066415 dated Apr. 7, 2010.
Goto, "Aqueous Layer, Tear Film Breakup Time, Tear Stability Analysis System," Journal of the Eye, vol. 22, No. 3, pp. 279-287, 2005 (English translation of pp. 279—Introduction and 280—Section II—But provided).
Maruyama et al., "The Environment and Dry Eye," Journal of the Eye, vol. 22, No. 3, pp. 311-316, 2005 (English translation of pp. 311—Introduction and 313—Section II—Contact Lens provided).

* cited by examiner

*Primary Examiner* — Patrick Lewis
*Assistant Examiner* — Everett White
(74) *Attorney, Agent, or Firm* — Birch, Stewart, Kolasch & Birch, LLP

(57) ABSTRACT

The present invention provides an ophthalmic composition which stabilizes the tear film during wearing contact lens, prevents eye dryness, imparts a favorable sensation in using, is highly convenient with no risk of misuse and shows a high efficiency in the course from manufacturing to sales. More specifically, the present invention provides a wetting solution—eye drops for contact lenses comprising (A) one or more member(s) selected from the group consisting of a cellulose-based polymer, a vinyl-based polymer, polyethylene glycol and dextran; and (B) one or more member(s) selected from the group consisting of chondroitin sulfate, alginic acid and salts thereof; and (C) a nonionic surfactant.

4 Claims, 1 Drawing Sheet

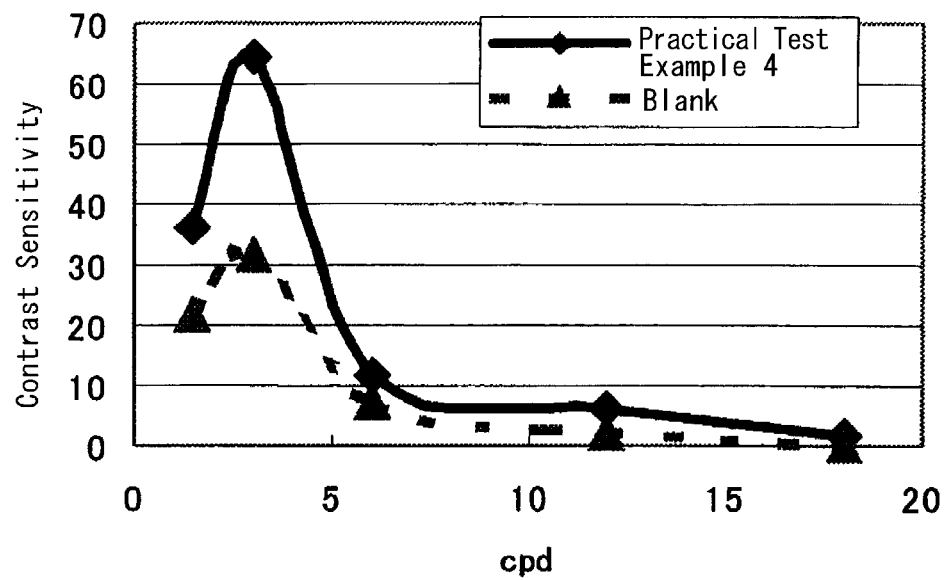

OPHTHALMIC COMPOSITION

TECHNICAL FIELD

The present invention relates to an ophthalmic composition for alleviating the influence of contact lens on eyes, more specifically to a wetting solution—eye drops for contact lenses, which is excellent, for example, in stabilization of tear film, particularly lipid layer, suppression of sensation of dryness and prevention of decline in visual function during wearing contact lens.

BACKGROUND ART

Recently, contact lens, particularly soft contact lens (hereinafter also referred to as SCL) have become very widely used for the purpose of vision correction or beauty. Wearing contact lens, however, places a load on the eye though it varies between individuals.

The typical complaint from contact lens users is eye dryness. A healthy tear film is a structure of thin layers with about 7 μm thickness, which is composed of three layers: mucin, aqueous and lipid layers from the eyeball side and protects cornea from drying, stimulation by external environment or the like. In particular, the lipid layer in the nearest position to the external environment prevents evaporation of tear fluid, however, due to the cause such as thinning or destabilization of tear film, the lipid layer is also prone to become thin, inhomogeneous, or unstable, and evaporation of tear fluid is promoted, and thus dry eye symptom including eye desiccation is occurred. And such destruction (destabilization) of tear film causes spots wherein the lipid layer is extremely thin or not existed. These spots observed on the surface of tear film is called dry spots, and the time elapsed until the appearance of dry spots can be used for calculating the tear film breakup time (BUT), accordingly, the dry spots is thought to be one of the important indexes for diagnostic criteria of eye desiccation or dry eye (see Journal of the eye, 22 (3): 279-287, 2005). Thus, it is of great significance if the time until the appearance of dry spots can be delayed or the increase in number and area of dry spots under the same time between blinks can be suppressed, because these lead to the suppression of dry eye symptom including eye desiccation or eye strain.

It has also been known that even if a person has healthy eyes without lenses, when he wears contact lenses the tear film becomes inhomogeneous and he easily feels desiccation of the eyes, thus he is susceptible to dry eye. In particular, while wearing SCL, the tear film on the SCL has a tendency to become very thin and thus there is a phenomenon observed in which the lipid layer often becomes extremely thin on the SCL or the lipid layer is sometimes partially or totally absent. As a result, evaporation of tear fluid is increased, and evaporation of water from inside the SCL and eventually from under the SCL is promoted, which may cause eye dryness or corneal disorder (see Journal of the eye, 22 (3): 311-316, 2005).

Therefore, in order to ensure safety for the eyes of contact lens users, it is necessary to stabilize the tear film on the outside of the lens, particularly, lipid layer continuously and effectively.

A method of applying artificial tears was conventionally taken to treat eye dryness, however, the method of only using artificial tears could not achieve stabilization of tear film, and thus a sufficient effect could not be obtained. Therefore, a system for stabilizing the tear film surrounding the contact lens was proposed in which polyvinylpyrrolidone is adsorbed on the surface of an ionic contact lens to increase water retention ability of the surface of the lens, and eye drops to the eye wearing a contact lens and a wetting solution used therefor were also proposed (JP 2001-247466 A). Furthermore, an ophthalmic liquid composition has been proposed in which long-chain alkyl derivatives of polysaccharides is used to promote and maintain the formation of trilaminar structure of tear film (JP 2007-77053 A). However, the systems and the compositions described in these documents have not sufficiently exerted an effect of stabilizing tear film, particularly lipid layer continuously and effectively.

Further, other problems associated with wearing contact lens include decreased contrast sensitivity. Contrast sensitivity is one of the criteria for evaluation of visual function, and it is a measure of the ability of distinguishing a slight difference of brightness. Decreased contrast sensitivity may lead, for example, to an accident because it is difficult for a person to distinguish the contrast between the road surface and obstacles while walking, or to an inconvenience in sports (especially, ball game) because it is difficult for a person to perceive the contrast between ball and background. It has been known that the decrease of contrast sensitivity is caused by an ophthalmic surgery such as keratorefractive surgery with the excimer laser, and aging, as well as wearing of contact lens. And there is a report that decrease of contrast sensitivity due to wearing of contact lens is associated with wearing of varifocal contact lens or soft contact lens for long term or use of extended-wear soft contact lens. As a solution to these problems, there is an attempt to change the contact lens itself, however, it has not been known that contrast sensitivity can be improved by an ophthalmic composition.

Meanwhile, ophthalmic solutions such as eye drops, eye washes or contact lens wetting solution have basically different purposes of use and they are handled independently in use. Thus, contact lens users are required to keep, for example, contact lens wetting solution and eye drops separately and use them independently. These solutions, however, are often similar in appearance because of the dosage and so on, despite of the difference in the purpose of use (application), therefore, there was a risk of misuse. For seller, there also was a risk of inducing misuses by consumers due to false recognition at providing information or mix-ups of products. Accordingly, there has been a wide demand from not only users but also sales persons for the development of products that can be used conveniently and safely with no risks of misuse.

DISCLOSURE OF THE INVENTION

Problems to be Solved by the Invention

As aforementioned, ophthalmic solutions such as eye drops and contact lens wetting solution have been handled independently. Although individual performance of these formulations has been studied, the suitability of the combination of eye drops and a contact lens wetting solution has not been sufficiently investigated. The present inventors have surprisingly found that when a contact lens is fitted with a conventional contact lens wetting solution, and then another eye drops is applied, the effects of sufficiently stabilizing the tear film, reducing eye strain and improving contrast sensitivity are not obtained, and even uncomfortable sensation in using such as a sensation of astringency or dryness may be produced.

Thus, an object of the present invention is to provide an ophthalmic composition that can stabilize the tear film during wearing contact lens and suppress eye dryness, and also resolve eye strain and decreased contrast sensitivity, and furthermore imparts a favorable sensation in using.

Another object of the present invention is to provide an ophthalmic composition that is highly convenient with no risk of misusage and is highly safe.

Still another object of the present invention is to provide an ophthalmic composition that shows a high efficiency and safety at any steps in the course from manufacturing, distribution to sales.

Means to Solve the Problem

As a result of intensive studies for solving the problems described above, the present inventors found that all the above mentioned problems can be solved by using a wetting solution—eye drops for contact lenses comprising (A) one or more compounds selected from the group consisting of a cellulose-based polymer, a vinyl-based polymer, polyethylene glycol and dextran; (B) one or more member(s) selected from the group consisting of chondroitin sulfate, alginic acid and salts thereof; and (C) a nonionic surfactant.

Thus, the present invention provides:

[1] A wetting solution—eye drops for contact lenses comprising (A) one or more member(s) selected from the group consisting of a cellulose-based polymer, a vinyl-based polymer, polyethylene glycol and dextran; (B) one or more member(s) selected from the group consisting of chondroitin sulfate, alginic acid and salts thereof; and (C) a nonionic surfactant.

[2] The wetting solution—eye drops for contact lenses as set forth in [1], wherein the component (A) is a cellulose-based polymer.

[3] The wetting solution—eye drops for contact lenses as set forth in [2], wherein the cellulose-based polymer is one or more member(s) selected from the group consisting of hydroxyethyl cellulose, hydroxypropylmethyl cellulose, and salts thereof.

[4] The wetting solution—eye drops for contact lenses as set forth in any one of [1] to [3], which comprises the component (A) in an amount of 0.0001 to 25 (w/v) %.

[5] The wetting solution—eye drops for contact lenses as set forth in any one of [1] to [4], wherein the component (B) is sodium chondroitin sulfate.

[6] The wetting solution—eye drops for contact lenses as set forth in any one of [1] to [5], which comprises the component (B) in an amount of 0.0005 to 10 (w/v) %.

[7] The wetting solution—eye drops for contact lenses as set forth in any one of [1] to [6], wherein the component (C) is one or more member(s) selected from the group consisting of polyoxyethylene sorbitan fatty acid esters, polyoxyethylene hydrogenated castor oil and polyoxyethylene-polyoxypropylene copolymer.

[8] The wetting solution—eye drops for contact lenses as set forth in any one of [1] to [7], wherein the component (C) is polysorbate 80.

[9] The wetting solution—eye drops for contact lenses as set forth in any one of [1] to [8], which comprises the component (C) in an amount of 0.001 to 5 (w/v) %.

[10] The wetting solution—eye drops for contact lenses as set forth in any one of [1] to [9], wherein the contact lens is a soft contact lens.

[11] The wetting solution—eye drops for contact lenses as set forth in [10], wherein the soft contact lens is essentially in soft contact lens Group IV.

[12] The wetting solution—eye drops for contact lenses as set forth in [10], wherein the soft contact lens is a soft contact lens made of silicone hydrogel.

[13] The wetting solution—eye drops for contact lenses as set forth in any one of [1] to [12] for suppressing eye desiccation or dry eye.

[14] The wetting solution—eye drops for contact lenses as set forth in any one of [1] to [12] for reducing eye strain or improving contrast sensitivity.

The Effect of the Invention

The wetting solution—eye drops for contact lenses of the present invention can efficiently stabilize the tear film during wearing contact lens, and can suppress eye dryness, eye strain, or contrast sensitivity decrease effectively.

The wetting solution—eye drops for contact lenses of the present invention also have an effect of reducing a stress on eyes caused by contact lens wearing. It is thought that eye dryness or eye strain during wearing contact lens is also related to the stress to corneal cells, and thus an effect of improving eye dryness or reducing eye strain by the wetting solution—eye drops for contact lenses of the present invention is accompanied with an effect of reducing the stress caused by wearing contact lens.

In addition, the wetting solution—eye drops for contact lenses of the present invention imparts a favorable sensation in using and it is not necessary to have a contact lens wetting solution and eye drops separately any more, and thus the solution is highly convenient and portable with no risk of misuse and it is safe as well.

Further, the wetting solution—eye drops for contact lenses of the present invention has an advantages including cost reduction in manufacturing stage, efficiency of transportation and display in distribution stage, such as reduction of transportation cost, and increase of safety in handling products in sales stage. Accordingly, the wetting solution—eye drops for contact lenses of the present invention can also contribute to the reduction of energy consumption, and is thus useful for energy saving, which means it can reduce the damage to the environment.

As described above, the present invention provides a wetting solution—eye drops, which exerts advantageous effects on achieving suppression of eye dryness, reduction of eye strain and improvement of contrast sensitivity during wearing contact lens, and is safe and convenient, and which can make it possible to secure safety and improve efficiency in the course from manufacturing to sales. Therefore the present invention can simultaneously achieve improvements of convenience and safety for the contact lens users, and efficiencies in each stage from manufacturing, transportation to sales.

BRIEF DESCRIPTION OF THE DRAWINGS

FIG. 1 is a graph which shows an improvement effect on the decreased contrast sensitivity during wearing contact lens by the wetting solution—eye drops for contact lenses of the present invention.

BEST MODES FOR CARRYING OUT THE INVENTION

The present invention is described in more detail below.

The following are definitions of terms used in this description, claims and drawing.

The term "fitting" as used herein represents action (or movement) of "putting a contact lens on an eye" and the term "wearing" as used herein represents the condition in which contact lens "exists on the cornea".

The term "%" as used herein represents w/v %, that is, the weight (g) of each component (solute) dissolved in 100 mL of solution unless otherwise indicated.

As used herein, the term "wetting solution—eye drops for contact lenses" represents ophthalmic composition which simultaneously has both functions as a contact lens wetting solution and as eye drops applicable during wearing contact lens. Further, the wetting solution—eye drops of the present invention is an ophthalmic composition wherein the same formulation can be used as a wetting solution when contact lens is fitted, and then can be used as eye drops to an eye with a contact lens. Throughout the specification, the term "wetting solution—eye drops for contact lenses" may be referred to only as "wetting solution—eye drops".

Further, the term "contact lens" as used herein is intended to encompass any types of contact lenses such as hard, oxygen permeable hard and soft contact lens, unless otherwise indicated.

Also the term "categories of soft contact lenses" as used herein represents SCL category based on the document titled "Regarding a Method of Classification of Soft Contact Lens" which is stipulated in the notification No. 645, "How to Deal with a Data to be Attached for Application for Manufacturing (Import) Approval of Soft Contact Lens and Disinfectant for Soft Contact Lens", Evaluation and Licensing Division, Pharmaceutical and Medical Safety Bureau-Ministry of Health, Labor and Welfare (former Ministry of Health and Welfare), Mar. 31, 1999. Among the categories, the SCL belonging to Group IV has a common property in which water content ratio is 50% or more and the ratio of mole % of monomers containing negative ion to constituent monomers of starting polymer in total is 1% or more. This classification follows the classification of soft contact lens established by FDA (U.S. Food and Drug Administration).

The term "essentially" is intended to include any soft contact lens which can be understood by one skilled in the art as being equal to those belonging to said category in the material, function and so on.

The contact lens made of silicone hydrogel material refers to a contact lens produced by using a material in which silicone-containing material (for example, TRIS which is a polymer of silicone with acrylate, or TRIS derivative) is copolymerized with hydrophilic monomer (for example, hydroxyethyl methacrylate, dimethylacrylamide), and the names of the materials according to USAN (United State Adopted Name) include, for example, LotrafilconA, LotrafilconB, BalafilconA, GalyfilconA, SenofilconA.

The wetting solution—eye drops for contact lenses according to the present invention is characterized by comprising (A) one or more compounds selected from the group consisting of a cellulose-based polymer, a vinyl-based polymer, polyethylene glycol and dextran; (B) one or more member(s) selected from the group consisting of chondroitin sulfate, alginic acid and salts thereof; and (C) a nonionic surfactant. The inclusion of these components can stabilize the tear film during wearing contact lens, thus can suppress eye dryness, therefore is effective for the reduction of eye strain and the improvement of contrast sensitivity and simultaneously enhance sensation of using. Also, when the same formulation of the present invention is used as a contact lens wetting solution and/or as eye drops, medicinal solutions with different properties do not have to be mixed on cornea and conjunctiva via contact lens. Although this mechanism has not been elucidated in detail yet, it is thought that the influence of the interaction between the medicinal solution and the contact lens on eyes or tear fluid might be minimized, and therefore the tear film can be kept to be stable, or eye strain can be reduced, contrast sensitivity can be improved, or the sensation of using can be enhanced as described above.

The wetting solution—eye drops for contact lenses of the present invention comprises one or more compounds selected from the group consisting of a cellulose-based polymer, a vinyl-based polymer, polyethylene glycol and dextran (hereinafter may be simply referred to as component (A)).

The cellulose-based polymer that can be used includes a cellulose-based polymer compound that can be obtained by substituting a hydroxyl group of the cellulose with other functional group and can give a viscosity to aqueous composition, and thus can be applicable to a contact lens. A functional group that may substitute the hydroxyl group of the cellulose includes methoxy group, ethoxy group, hydroxymethoxy group, hydroxyethoxy group, hydroxypropoxy group, carboxymethoxy group, carboxyethoxy group and the like. Typical examples of the cellulose-based polymer include methylcellulose, ethylcellulose, hydroxyethyl cellulose, hydroxymethyl cellulose, hydroxypropyl cellulose, hydroxypropylmethyl cellulose, carboxymethyl cellulose, carboxyethyl cellulose and salts thereof. Such salts are preferably pharmacologically acceptable salts, among which alkali metal salts are more preferred, and the salt such as sodium salt or potassium salt is particularly preferred. Although there is no limitation on the substitution degree of substituents or the molecular weight of the cellulose-based polymer used in the present invention, said polymer may have a weight-average molecular weight of, for example, about 5000 to 1,000,000, preferably about 10,000 to 500,000 and more preferably about 10,000 to 100,000. These cellulose-based polymers are commercially available, and may be used alone or in any combination of two or more types thereof. From the viewpoint of further enhancing the effect of the invention, the cellulose-based polymers are one or more compounds preferably selected from the group consisting of methylcellulose, hydroxyethyl cellulose, hydroxypropylmethyl cellulose, hydroxypropyl cellulose, carboxymethyl cellulose and salts thereof. More preferred examples include hydroxypropylmethyl cellulose, hydroxyethyl cellulose and carboxymethylcellulose sodium, and particularly preferred examples are hydroxypropylmethyl cellulose or hydroxyethyl cellulose.

The content of the cellulose-based polymer in the wetting solution—eye drops for contact lenses of the present invention, is not limited because the content also varies depending on the kind of the compound or the molecular weight thereof, but is usually 0.0001 to 25%, preferably 0.001 to 10%, more preferably 0.001 to 7%, even more preferably 0.005 to 5%, particularly preferably 0.01 to 1% as a ratio of the total amount of these compounds to the total amount of the wetting solution—eye drops for contact lenses.

The vinyl-based polymer that can be used includes a polymer that can give a viscosity to aqueous composition, and thus can be applicable to a contact lens. Typical examples of the vinyl-based polymer include vinyl alcohol polymer such as polyvinyl alcohol (completely or partially saponified), vinyl pyrrolidone polymer such as polyvinylpyrrolidone, and carboxy vinyl polymer and so on. Although there is no limitation in the molecular weight of the vinyl-based polymer used herein, the vinyl-based polymer may have a weight-average molecular weight of, for example, about 5,000 to 1,000,000, preferably about 10,000 to 500,000 and even more preferably about 10,000 to 400,000. These vinyl-based polymers are commercially available, and may be used alone or in any combination of two or more types thereof. From the viewpoint of further enhancing the effect of the invention, polyvinylpyrrolidone K25, polyvinylpyrrolidone K30, polyvinylpyrrolidone K90, polyvinyl alcohol (partially saponified) and carboxy vinyl polymer are preferred, polyvinyl alcohol (partially saponified) and carboxy vinyl polymer are more preferred, and polyvinyl alcohol (partially saponified) is particularly preferred.

The content of the vinyl-based polymer in the wetting solution—eye drops for contact lenses of the present invention is not limited because the content also varies depending on the kind of the compound or the molecular weight thereof, but is usually 0.001 to 25%, preferably 0.001 to 10%, more preferably 0.005 to 5%, even more preferably 0.01 to 5%, particularly preferably 0.1 to 3% as a ratio of the total amounts of these compounds to the total amounts of the wetting solution—eye drops for contact lenses.

Dextran is a water-soluble polymer compound that can be obtained by partially hydrolyzing a polysaccharide that is produced from sucrose as a starting material by certain lactic acid bacteria. The dextran that can be used in the present invention may have a weight-average molecular weight of about 5,000 to 1,000,000, preferably about 10,000 to 500,000 and more preferably about 10,000 to 100,000. These dextrans are commercially available, and may be used alone or in any combination of two or more types thereof. From the viewpoint of further enhancing the effect of the invention, dextran, dextran 70 and dextran 40 are preferred, and dextran 70 is particularly preferred.

The content of the dextran in the wetting solution—eye drops for contact lenses of the present invention is usually 0.001 to 25%, preferably 0.001 to 10%, more preferably 0.01 to 10%, even more preferably 0.01 to 5%, particularly preferably 0.01 to 1%, further particularly preferably 0.01 to 0.1% as a ratio of the total amount of these dextrans to the total amount of the wetting solution—eye drops for contact lenses.

Polyethylene glycol that may be used in the present invention is also referred to as macrogol. Although there is no limitation on the substitution degree of substituents or the molecular weight of the polyethylene glycol, the weight-average molecular weight of the polyethylene glycol may be about 100 to 50,000, preferably about 400 to 20,000 and more preferably about 2000 to 10,000. Also, these polyethylene glycols are commercially available and may be used alone or in any combination of two or more types thereof. Among them, from the viewpoint of further enhancing the effect of the invention, macrogol 6000, macrogol 4000 and macrogol 400 are preferred, and macrogol 6000 and macrogol 4000 are particularly preferred.

The content of polyethylene glycol in the wetting solution—eye drops for contact lenses of the present invention is usually 0.001 to 25%, preferably 0.001 to 10%, more preferably 0.01 to 10%, even more preferably 0.05 to 5%, particularly preferably 0.05 to 2% as a ratio of the total amount of these polyethylene glycols to the total amount of the wetting solution—eye drops for contact lenses.

The component (A) of the present invention can be used alone or in any combination of two or more types thereof. From the viewpoint of further enhancing the effect of the invention, the component (A) is preferably a cellulose-based polymer, among which, hydroxypropyl methylcellulose and hydroxyethyl cellulose are particularly preferable.

The content of the component (A) in the wetting solution—eye drops for contact lenses of the present invention is usually 0.0001 to 25%, preferably 0.001 to 10%, more preferably 0.005 to 10%, further preferably 0.01 to 7%, particularly preferably 0.01 to 5% as a ratio of the total amount of these (A) components to the total amount of the wetting solution—eye drops for contact lenses.

The wetting solution—eye drops for contact lenses of the present invention further comprises one or more member(s) selected from the group consisting of chondroitin sulfate, alginic acid and salts thereof (hereinafter may be simply referred to as component (B)).

When chondroitin sulfate or salt thereof is used, they may be used either a natural product or synthetic product. Although there is no limitation on the molecular weight thereof used in the present invention, preferably about five thousand to fifty thousand, more preferably about ten thousand to forty thousand, further preferably about fifteen thousand to thirty-five thousand. The chondroitin sulfate or salt thereof are also commercially available. The salt of chondroitin sulfate includes for example, sodium salt or potassium salt, but is not limited thereto. Sodium chondroitin sulfate is preferred. The chondroitin sulfate or salt thereof may be used alone or in any combination of two or more types thereof.

The content of the chondroitin sulfate or salt thereof in the wetting solution—eye drops for contact lenses of the present invention, is not limited because the content also varies depending on the molecular weight thereof, but is usually 0.0005 to 10%, preferably 0.0005 to 5%, more preferably 0.001 to 3%, particularly preferably 0.001 to 1% as a ratio of the total amount of these compounds to the total amount of the wetting solution—eye drops for contact lenses.

When alginic acid or salt thereof is used, they may be used either a natural product or synthetic product. The alginic acid or salt thereof can be used without limiting a ratio of mannuronic acid/guluronic acid (M/G ratio) thereof, but is preferably 4.0 and less, more preferably 3.0 and less, further preferably 2.5 and less, particularly preferably 2.0 and less. Although there is no limitation on the molecular weight thereof used in the present invention, said they may have a weight-average molecular weight of, about five thousand to one million, preferably about ten thousand to half one million, further preferably about ten thousand to one hundred thousand. The alginic acid or salt thereof are also commercially available. The salt of alginic acid includes for example, sodium salt or potassium salt, but is not limited thereto. Sodium alginate is preferred. The alginic acid or salt thereof may be used alone or in any combination of two or more types thereof.

The content of the alginic acid or salt thereof in the wetting solution—eye drops for contact lenses of the present invention is usually 0.001 to 5%, more preferably 0.005 to 5%, further preferably 0.005 to 1%, particularly preferably 0.01 to 0.5% as a ratio of the total amount of these compounds to the total amount of the wetting solution—eye drops for contact lenses.

The (B) component of the present invention is all acid mucopolysaccharides, and may be used alone or in any combination of two or more types thereof. From the viewpoint of further enhancing the effect of the invention, the component (B) is preferably sodium chondroitin sulfate, alginic acid or sodium alginate, more preferably sodium chondroitin sulfate.

The content of the component (B) in the wetting solution—eye drops for contact lenses of the present invention is usually 0.0005 to 10%, preferably 0.001 to 7%, more preferably 0.005 to 5%, further preferably 0.01 to 3%, particularly preferably 0.01 to 1% as a ratio of the total amount of these (A) components to the total amount of the wetting solution—eye drops for contact lenses.

In addition, the wetting solution—eye drops for contact lenses of the present invention further comprises an appropriate nonionic surfactant (hereinafter may be simply referred to as component (C)).

The nonionic surfactant used in the present invention can include the surfactants which can be applied to an ophthalmic composition for contact lens by those skilled in the art, for example, polyoxyethylene-polyoxypropylene block copolymer (hereinafter also referred to as polyoxyethylenepolyoxypropylene copolymer) such as poloxamer 407, poloxamer 235 and poloxamer 188; POE-POP block copolymer adduct of ethylene diamine such as poloxamine; POE sorbitan fatty acid esters such as monolaurate POE (20) sorbitan (polysorbate 20), POE (20) sorbitan monooleate (polysorbate 80), POE sorbitan monostearate (polysorbate 60), POE sorbitan tristearate (polysorbate 65); POE hydrogenated castor oils such as POE hydrogenated castor oil 5, POE hydrogenated castor oil 10, POE hydrogenated castor oil 20, POE hydrogenated castor oil 40, POE hydrogenated castor oil 50, POE hydrogenated castor oil 60, POE hydrogenated castor oil 100; POE alkyl ethers such as POE (9) lauryl ether; POE POP alkyl ethers such as POE (20) POP (4) cetyl ether; POE alkyl phenyl ethers such as POE (10) nonylphenyl ether. Here, POE represents polyoxyethylene, POP represents polyoxypropylene and the figures shown in the parentheses represent the number of added moles.

Among them, polyoxyethylene-polyoxypropylene block copolymer, POE sorbitan fatty acid esters and POE hydrogenated castor oils are preferable, and poloxamer 407, polysorbate 80 and POE hydrogenated castor oil 60 are particularly preferable.

The content of the nonionic surfactant in the wetting solution—eye drops for contact lenses of the present invention cannot be uniformly defined since the content varies depending on the kind of the surfactant and the like, but is usually 0.001 to 5%, preferably 0.001 to 1.5%, more preferably 0.001 to 1%, even more preferably 0.005 to 0.5%, particularly preferably 0.05 to 0.3% as a ratio of the total amount of these surfactants to the total amount of the wetting solution—eye drops for contact lenses.

Preferably, the wetting solution—eye drops for contact lenses of the present invention comprises appropriate buffering agents, if desired. The buffering agents used in the present invention include borate buffering agent, phosphate buffering agent, carbonate buffering agent, citrate buffering agent, acetate buffering agent, HEPES buffering agent, MOPS buffering agent and the like. More specific examples of the buffering agents include a compound selected from the group consisting of boric acid, sodium borate, potassium tetraborate, borax, potassium metaborate, phosphoric acid, disodium hydrogen phosphate, sodium dihydrogen phosphate, potassium dihydrogen phosphate, carbonic acid, sodium bicarbonate, sodium carbonate, citric acid, sodium citrate, potassium citrate, acetic acid, sodium acetate, HEPES, MOPS, and hydrates thereof, and a combination of two or more compounds selected from the above agents.

Preferred examples of the buffering agents include borate buffering agent, phosphate buffering agent, carbonate buffering agent and citrate buffering agent. Particularly preferred buffering agents are borate buffering agent or phosphate buffering agent. More specifically, particularly preferred buffering agents include borate buffering agents, for example, boric acid, borate such as alkaline metal borate and alkaline earth metal borate, and a combination of boric acid and borate, with boric acid or borax being particularly preferred, and phosphate buffering agents, for example, phosphoric acid, phosphate such as alkaline metal phosphate or alkaline earth metal phosphate, hydrates thereof, and a combination of phosphoric acid and phosphate, with disodium hydrogen phosphate, sodium dihydrogen phosphate and hydrates thereof being particularly preferred.

The content of the buffering agent in the wetting solution—eye drops for contact lenses of the present invention cannot be uniformly defined, since the content varies depending on the kind of the buffering agent and the like, but is usually 0.001 to 5%, preferably 0.001 to 3%, more preferably 0.005 to 2%, even more preferably 0.005 to 1.5%, particularly preferably 0.05 to 1.5% as a ratio of the total amount of these buffering agents to total amounts of the wetting solution—eye drops for contact lenses.

Preferably, the wetting solution—eye drops for contact lenses of the present invention comprises an appropriate inorganic salt, if desired. The inorganic salts include potassium chloride, sodium chloride, sodium bicarbonate and sodium carbonate, and may be used alone or in any combination of two or more types thereof.

The content of inorganic salt in the wetting solution—eye drops for contact lenses of the present invention cannot be uniformly defined since the content varies depending on the kind of the inorganic salt and the like, but is usually 0.001 to 5%, preferably 0.01 to 1.5%, more preferably 0.1 to 0.7% as a ratio of the total amount of these inorganic salts to the total amount of the wetting solution—eye drops for contact lenses.

Preferably, the wetting solution—eye drops for contact lenses of the present invention comprises an appropriate ethylenediamine acetic acid derivative or a salt thereof, if desired. Typical examples of the ethylenediamine acetic acid derivative or salts thereof include edetic acid (ethylenediaminetetraacetic acid, EDTA), ethylenediaminediacetic acid (EDDA), diethylenetriaminepentaacetic acid (DTPA), N-(2-hydroxyethyl)ethylenediaminetriacetic acid (HEDTA) or salts thereof. The salt of ethylenediamine acetic acid derivative includes a pharmacologically or physiologically acceptable salt, for example, a salt with alkaline metal (sodium, potassium or the like) or a salt with alkaline-earth metal (calcium, or the like). Among them, ethylenediaminetetraacetic acid or a salt thereof, such as ethylenediaminetetraacetate calcium disodium, ethylenediaminetetraacetate disodium or ethylenediaminetetraacetate disodium.dihydrates (hereinafter also referred to as sodium edetate) are preferred, and ethylenediaminetetraacetate disodium.dihydrates is particularly preferred. These can be used alone or in any combination of two or more thereof.

The content of ethylenediamine acetic acid derivative or a salt thereof in the wetting solution—eye drops for contact lenses of the present invention cannot be uniformly defined since the content varies depending on the molecular weight, the kind thereof or the like, but is preferably 0.0001 to 1%, more preferably 0.0005 to 0.5%, even more preferably 0.001 to 0.3%, particularly preferably 0.001 to 0.05% as a ratio of the total amount of these ethylenediamine acetic acid derivatives or salts thereof to the total amount of the wetting solution—eye drops for contact lenses.

Also from the viewpoint of further enhancing the effect of the invention, it is more preferred that the wetting solution—eye drops for contact lenses of the present invention comprises an derivative of ethylenediamineacetic acid or a salt thereof, a nonionic surfactant, an inorganic salt and a buffering agent in combination.

The content of ethylenediamine acetic acid derivative or a salt thereof, inorganic salt or buffering agent in the wetting solution—eye drops for contact lenses of the present invention is preferably 0.01 to 5%, particularly preferably 0.05 to 3%, as a ratio of the total amount of these components to the total amount of the wetting solution—eye drops for contact lenses.

Preferably, the wetting solution—eye drops for contact lenses of the present invention is used particularly for soft contact lens in a group of contact lens. This is because soft contact lens is prone to cause a feeling of dryness and thus puts a strain on eyes. And also because it is useful for soft contact lens with high moisture content, which is specifically prone to cause a feeling of dryness, particularly for soft contact lens of SCL Group IV. In addition, unexpectedly, the wetting solution—eye drops for contact lenses of the present invention shows remarkable advantageous effect on the soft contact lens made of silicone-hydrogel, and is thus preferably used for said soft contact lens.

The wetting solution—eye drops for contact lenses of the present invention is appropriate for comprising various components (including pharmacologically-active component or physiologically-active component) in combination with each other. Decongestants, drugs for modulating ocular muscles, anti-inflammatory drugs or astringents, antihistamine drugs or antiallergic drugs, vitamins, amino acids or local anesthetics usually used for ophthalmic composition or the like can be exemplified. Specifically, the following components can be exemplified.

Decongestants: for example, α-adrenergic drugs such as epinephrine, epinephrine hydrochloride, ephedrine hydrochloride, oxymetazoline hydrochloride, tetrahydrozoline hydrochloride, naphazoline hydrochloride, phenylephrine hydrochloride, methylephedrine hydrochloride, epinephrine bitartrate, naphazoline nitrate or the like, all of which may be any form of d-form, l-form or dl-form;

Drugs for modulating ocular muscles: for example, cholinesterase inhibitor with active centers similar to that of acetylcholine, such as neostigmine methylsulfate, tropicamide, helenien atropine sulfate or the like;

Anti-inflammatory drugs or astringents: for example, zinc sulfate, zinc lactate, allantoin, ε-aminocaproic acid, indomethacin, lysozyme chloride, silver nitrate, pranoprofen, sodium azulene sulfonate, dipotassium glycyrrhizinate, diclofenac sodium, bromfenac sodium, berberine chloride, berberine sulfate or the like;

Antihistamine drugs or Antiallergic drugs: for example, acitazanolast, amlexanox, ibudilast, tranilast, diphenhydramine hydrochloride, levocabastine hydrochloride, ketotifen fumarate, sodium cromoglycate, pemirolast potassium, chlorpheniramine maleate or the like;

Vitamins: for example, retinol acetate, retinol palmitate, pyridoxine hydrochloride, sodium flavin adenine dinucleotide, pyridoxal phosphate, cyanocobalamin, panthenol, calcium pantothenate, sodium pantothenate, ascorbic acid, tocopherol acetate or the like;

Amino acids: for example, potassium aspartate, sodium aspartate, magnesium and potassium aspartate, glutamic acid, sodium glutamate, aminoethylsulfonic acid or the like;

Local anesthetics: for example, chlorobutanol, oxybuprocaine hydrochloride, cocaine hydrochloride, cornecaine hydrochloride, dibucaine hydrochloride, tetracaine hydrochloride, diethylaminoethyl p-butylaminobenzoate hydrochloride, piperocaine hydrochloride, procaine hydrochloride, proparacaine hydrochloride, hexothiocaine hydrochloride, lidocaine hydrochloride or the like;

Also various component or additives can be selected appropriately within the range of not being adversely affected, depending on use or form, according to a conventional method and then one or more kind of thereof may be contained in the wetting solution—eye drops for contact lenses of the present invention. These components or additives includes for example, carrier that be usually used for preparation of semi-solid formulation or liquid formulation (for example, water, aqueous solvent or aqueous or oily base or the like), or a variety of additives such as thickener, saccharides, sugar alcohols, acid mucopolysaccharides, surfactant, preservatives, disinfectants or antibacterial drugs, pH adjusters, tonicity agents, flavors or refrigerants, and stabilizers or the like.

The representative examples of component that used in the wetting solution—eye drops for contact lenses of the present invention are the following ones, but not limited thereto; i.e.

Saccharides: for example, glucose, cyclodextrin;
Sugar alcohols: for example, xylitol, sorbitol, mannitol;
Acid mucopolysaccharides: alginic acid, sodium alginate;
Surfactant: for example, surfactants other than the nonionic surfactant as aforementioned, for example, glycin type-ampholytic surfactant such as alkyldiaminoethylglycine; alkyl tetraalkylammonium salts (for example, cationic surfactant such as benzalkonium chloride, benzethonium chloride);

Preservatives, Disinfectants or Antibacterial drugs: for example, alkyldiaminoethylglycine hydrochloride, sodium benzoate, ethanol, benzalkonium chloride, benzethonium chloride, chlorhexidine gluconate, chlorobutanol, sorbic acid, potassium sorbate, sodium dehydroacetate, methyl parahydroxybenzoate, ethyl parahydroxybenzoate, propyl parahydroxybenzoate, butyl parahydroxybenzoate, oxyquinoline sulfate, phenethyl alcohol, benzyl alcohol, biguanide (for example, polyhexamethylene biguanide or hydrochloride salt thereof), polidronium chloride, Glokill® (Rhodia) or the like;

pH adjusters: for example, hydrochloric acid, boric acid, epsilon-aminocaproic acid, acetic acid, sodium hydroxide, sodium bicarbonate, sodium carbonate, borax, triethanolamine, monoethanolamine or the like;

Tonicity agents: for example, sodium hydrogen sulfite, sodium sulfite, magnesium chloride, potassium acetate, sodium acetate, sodium thiosulfate, magnesium sulfate, glycerin, propylene glycol or the like;

Stabilizers: for example, dibuthyl hydroxytoluene, trometamol, sodium formaldehyde sulfoxylate (Rongalite), tocopherol, sodium pyrosulfite, monoethanolamine, aluminum monostearate or the like;

Flavors or refrigerants: for example, terpenoid (for example, anethol, eugenol, camphor, geraniol, cineol, borneol, menthol, limonen, or the like, all of which may be in either d-form, l-form or dl-form), essential oil (fennel oil, cool mint oil, cinnamon oil, spearmint oil, mentha water, mentha oil, peppermint oil, bergamot oil, eucalyptus oil, rose oil, etc.) or the like.

The viscosity of the wetting solution—eye drops for contact lenses of the present invention can be initially adjusted at an appropriate level in order to obtain a desired effect and the level can be maintained stably for extended period. When the viscosity of the ophthalmic composition for contact lens is set, the viscosity value at 20° C. is preferably designed to maintain 1.1 mPa·s or more, and can be designed to be usually 1.1 to 300 mPa·s, preferably 1.3 to 100 mPa·s, particularly preferably 1.5 to 80 mPa·s.

Viscosity can be measured according to a method with the rotational viscometer of cone-plate type (a method described in 45. Viscosity Determination, Method II Viscosity measurement by rotational viscometer, "(3) Cone-flat plate-type rotational viscometer" in General Tests, The Japanese Pharmacopoeia Fourteenth Edition), specifically, it can be measured by a commercially available rotational viscometer of cone-plate type and an appropriately selected rotor. For example, the viscosity at 20° C. can be measured by using commercially available viscometer of type E (manufactured by TOKIMEC Inc. and supplied by TOKI SANGYO, Co., Ltd., Japan) and an appropriately selected rotor, and by calibrating with petroleum-derived hydrocarbon oil (Newtonian fluid) that is defined by JIS (Japanese Industrial Standards) Z8809 as a calibrating standard for each determination of the test samples. Specifically, the viscosity is measured according to the viscosity determination described in JP 2006-348055 A (the condition of measurement is described below).

The wetting solution—eye drops for contact lenses of the present invention is adjusted to have an osmolality within the biologically acceptable range, if desired. The osmolality is usually 0.3 to 4.1, preferably 0.4 to 4.1, more preferably 0.3 to 2.1, particularly preferably 0.5 to 1.4 as an osmolality ratio to that of physiological saline. The osmolality ratio is measured by referring to the method described in Osmolality Determination, in General Tests, The Japanese Pharmacopoeia Fifteenth Edition.

The pH of the wetting solution—eye drops for contact lenses of the present invention is adjusted to a value within the range to make the solution of the present invention applicable to human body, if desired. The pH is usually 4.0 to 9.0, preferably 5.0 to 8.5, particularly preferably 5.5 to 8.5. The pH can be adjusted with a buffering agent or a pH adjuster as described above.

The wetting solution—eye drops for contact lenses of the present invention can be prepared by a known method in the art, and a step of filtration sterilization, a step of filling the solution in a container, or the like may be included, if desired.

The method of using the wetting solution—eye drops for contact lenses of the present invention includes for example, a method of [the use at the time of fitting a contact lens (just before fitting) by dropwise adding the wetting solution—eye drops for contact lenses directly to a contact lens, wetting both sides or one side of the contact lens with an appropriate amount thereof (for example, suitably, one or two drop(s) for one time), and then fitting said contact lens] (the use explained in the parenthesis may be also described as "usage as a contact lens wetting solution"). Also included a method of [the use during wearing a contact lens by applying an appropriate amount (for example, suitably, one or two drop (s) for one time) of the wetting solution—eye drops for contact lenses to eyes (the use explained in the parenthesis may also be described as "usage as eye drops"). The number of instillation into eyes for a day is not limited, but is normally in a range of 1 to 10 times, preferably from 1 to 6 times, particularly preferably from 5 to 6 times.

The particularly recommended usage of the wetting solution—eye drops for contact lenses is the usage wherein the interval between the use as a contact lens wetting solution as described above and the first application to eyes after fitting the contact lens is within 5 hours, preferably 2 hours, more preferably 1 hour, even more preferably 30 minutes, particularly preferably 10 minutes, further particularly preferably 2 minutes. The application thereafter is carried out similarly to the usual usage of eye drops.

The present invention may further comprises the following steps of handling contact lens: (1) a step of adding dropwise the wetting solution—eye drops for contact lenses directly to a contact lens in order to wet both sides or one side of the contact lens with an appropriate amount thereof (for example, suitably, one or two drop(s) for one time) when fitting a contact lens (just before fitting); (2) a step of fitting a contact lens to an eye; (3) a step of wetting a contact lens by applying said solution to an eye during wearing the contact lens. Also, the present invention may comprise the following steps of handling contact lens: (4) a step of applying said solution to an eye to wet a contact lens when removing the contact lens (just before removing); (5) a step of removing a contact lens from an eye; (6) a step of applying the wetting solution—eye drops for contact lenses to an eye just before fitting a contact lens). For handling contact lens, an appropriate step may be selected from the above steps, if desired.

In the meanwhile, from the viewpoint of further enhancing the effect of the invention, it is the target of the invention to subject the wetting solution—eye drops for contact lenses preferably to the both usage as a contact lens wetting solution and usage as eye drops while wearing contact lens, however the solution of the invention can also be for either use only.

EXAMPLES

The present invention is illustrated in more detail by Test Examples and Examples, but should not be construed to be limited thereto.

In Test Examples, the tests were conducted as successively as possible to keep the measuring condition, in particular the subject's condition almost constant. Each Test Example was carried out independently.

The viscosities in each Example and Comparative Example were determined by using TVE-20L cone-plate type viscometer (manufactured by TOKIMEC Inc. and supplied by TOKI SANGYO, Co., Ltd., Japan), which is a kind of E-type viscometer, under the following measuring condition according to the manufacturer's instructions. Unless stated otherwise, the measurement was carried out according to the viscometric determination described in JP A 2006-348055. The measuring condition used was as follows.

Measuring Condition:
 Rotor used: standard rotor (1° 34', R=2.4 cm)
 Rotational frequency: 100 rpm (the viscosity is measured at the highest rotational frequency among the measurable rotation frequencies depending on each formulation since the acceptable range of rotational frequency is different depending on the viscosity.)
 Amount of sample: 1 mL
 Temperature: 20° C.
 Time: The viscosity after 3 minutes was defined as the measurement.

Test 1: Evaluation with Dry Eye Observation Instrument (DR-1, Kowa Company, Ltd.)
(Test Method)

Each wetting solution—eye drops for contact lenses of Examples 1 to 6 and Comparative Examples 1 to 3 was prepared by the formulation of Table 1 according to a usual preparative method (conventional method) of eye drops and others, and was filled into a polyethylene terephthalate container (volume: 10 mL) and plugged with a nozzle and a cap. Soft contact lens (trade name: Ciba Vision K.K., soft contact lens Group I (silicone-hydrogel lens, main material: LotrafilconA) (hereinafter also referred to as "SCL1") and a soft contact lens (trade name: Johnson & Johnson K.K., soft contact lens Group IV (main material: EtafilconA) (hereinafter also referred to as "SCL2") were used. After wetting both sides of these contact lenses with one drop of the wetting solution—eye drops of each formulation, the contact lenses were fitted, and at two minutes after the fitting, the wetting solution—eye drops of the same formulation was applied to eyes.

Thereafter, an evaluation was carried out according to the condition of each test (1) to (3). Three subjects were selected from persons who usually wore contact lenses and had a sensation of dryness (persons who are prone to dry eye). After a subject was examined with a kind of testing solution, he rested his eyes sufficiently, and then he was examined with the next testing solution.

(1) Evaluation of the Area of Dry Spot-1

The wetting solution—eye drops for contact lenses was subjected to the usage as a contact lens wetting solution under the condition as described above, and then, the solution was applied to eyes while wearing contact lenses, followed by the evaluation of the number and size of dry spot under the following condition.

The dry spot was observed on a dry eye observation instrument (DR-1, Kowa Company, Ltd.) which was used for observation of an interference color of the tear fluid lipid layer. Specifically, the number and the size of dry spots on the eye surface was measured at one second after the beginning of a blinking observed at about two minutes after the application to eyes.

Analysis A:

The dry spots observed for each wetting solution—eye drops for contact lenses of Example 1 and Comparative Examples 1 to 3 were divided into three kinds of the size according to Table 2, and then the number of the spots of each size was counted. The score for each size in Table 2 was multiplied by the number of the spots. At last, subtotal of the score for each size was summed to obtain "the total score of dry spot" for each formulation. The average "total score of dry spot" for three subjects was evaluated according to Table 3 and the result was shown in Table 4.

Analysis B:

For each dry spot observed for each wetting solution—eye drops for contact lenses of Examples 1 to 5 and Comparative Examples 1 to 3, the area value was calculated from the image obtained and then a sum of the area value was calculated as a total area for each formulation. Thereafter, the results of the three subjects were averaged, and each relative value of the total area for each formulation of Examples and Comparative Examples was calculated by defining the total area of Example 1 as the value of 1, and the result was shown in Table 5 as "relative evaluation of the total area of dry spot".

TABLE 2

| Criteria | Score |
| --- | --- |
| Diameter under 0.1 mm | 1 point |
| Diameter 0.1 mm and more, under 0.2 mm | 2 points |
| Diameter 0.2 mm and more | 3 points |

TABLE 3

| Total score of dry spot | Evaluation of total score of dry spot |
| --- | --- |
| 41 points and more | not good |
| 31 points to 40 points | moderate |
| 21 points to 30 points | good |
| 20 points and less | very good |

TABLE 4

| | Evaluation of total score of dry spot | | | |
| --- | --- | --- | --- | --- |
| Soft contact lens | Ex. 1 | Comp. 1 | Comp. 2 | Comp. 3 |
| SCL1 | very good | not good | moderate | not good |
| SCL2 | very good | not good | good | moderate |

TABLE 5

| Soft contact lens | Evaluation for total score of dry spot | | | | | | | |
| --- | --- | --- | --- | --- | --- | --- | --- | --- |
| | Ex. 1 | Comp. 1 | Comp. 2 | Comp. 3 | Ex. 2 | Ex. 3 | Ex. 4 | Ex. 5 |
| SCL1 | 1.0 | 13.0 | 12.8 | 15.2 | 1.9 | 3.6 | 4.6 | 5.8 |
| SCL2 | 1.0 | 36.1 | 13.0 | 26.2 | 3.3 | 5.8 | 9.1 | 11.1 |

TABLE 1

| | Ex. 1 | Comp. 1 | Comp. 2 | Comp. 3 | Comp. 4 | Ex. 2 | Ex. 3 | Ex. 4 | Ex. 5 |
| --- | --- | --- | --- | --- | --- | --- | --- | --- | --- |
| HPMC[1] | 0.2 | 0.2 | 0.2 | — | — | 0.2 | — | — | — |
| polyvinyl pyrrolidone K90 | — | — | — | — | — | — | 2.5 | — | — |
| macrogol 4000 | — | — | — | — | — | — | — | 1 | — |
| dextran 70 | — | — | — | — | — | — | — | — | 1 |
| sodium chondroitin sulfate | 0.5 | 0.5 | — | 0.5 | — | — | 0.3 | 0.1 | 0.05 |
| alginic acid | — | — | — | — | — | 0.05 | — | — | — |
| sodium chloride | 0.44 | 0.44 | 0.44 | 0.44 | 0.44 | 0.44 | 0.44 | 0.44 | 0.44 |
| potassium chloride | 0.08 | 0.08 | 0.08 | 0.08 | 0.08 | 0.08 | 0.08 | 0.08 | 0.08 |
| polysorbate 80 | 0.05 | — | 0.05 | 0.05 | — | 0.05 | 0.05 | 0.05 | 0.05 |
| boric acid | 1.0 | 1.0 | 1.0 | 1.0 | 1.0 | 1.0 | 1.0 | 1.0 | 1.0 |
| borax | 0.2 | 0.2 | 0.2 | 0.2 | 0.2 | 0.2 | 0.2 | 0.2 | 0.2 |
| edetate sodium | 0.05 | 0.05 | 0.05 | 0.05 | 0.05 | 0.05 | 0.05 | 0.05 | 0.05 |
| purified water | q.s. | q.s. | q.s. | q.s. | q.s. | q.s. | q.s. | q.s. | q.s. |
| total volume | 100 mL | 100 mL | 100 mL | 100 mL | 100 mL | 100 mL | 100 mL | 100 mL | 100 mL |
| pH | 7.3 | 7.3 | 7.3 | 7.3 | 7.3 | 7.3 | 7.3 | 7.3 | 7.3 |
| osmolality ratio | 1.2 | 1.2 | 1.2 | 1.2 | 1.2 | 1.2 | 1.2 | 1.3 | 1.2 |

[1] Hydroxypropyl methylcellulose 2906 (trade name: 65SH-4000 (Shin-Etsu Chemical. Co., Ltd.)

Dry spot is recognized as an index representing dry eye or desiccation of eye in the opthalmologic field. Accordingly, if the initiation time of dry spot (the time elapsed until the appearance of dry spot) is short, many dry spots are observed, the size of dry spot is large, or the like, it can be said that the eye is more dried. The result of this test showed that the total areas of dry spot for the formulations of Examples were remarkably smaller than those for the formulations of Comparative Examples. Thus, by the formulations of Examples, it can be said that the tear film on the surface of contact lens was stabilized and dry spot was difficult to form. Also, this fact showed that desiccation of eye was suppressed remarkably, thus a symptom of dry eye was improved.

(2) Evaluation of the Area of Dry Spot-2

The wetting solution—eye drops for contact lenses was subjected to the usage as a contact lens wetting solution under the condition as described above, and then, the solution was applied to eyes while wearing contact lenses, followed by the evaluation of the area of dry spot under the following condition.

In the dry eye observation instrument (DR-1), the area of the dry spot of the maximum size, which was observed between the beginning of a blinking at about 11 minutes after the application to eyes and the beginning of the next blinking was analyzed by the image analyzer, and then the area ratio (%) to the whole area observed on the eye surface was calculated. About 11 minutes after the application of eye drops, eye dryness was progressed especially in the case of the formulations of Comparative Examples and thus dry spot was observed as a single comprehensive form of dry area. The average total score of the three subjects and a relative value of an area ratio for each formulation was calculated by defining the area ratio of Example 1 as the value of 1. The result is shown in Table 6 as "Evaluation-2 for the Area of Dry Spot".

observation instrument (DR-1), and then was evaluated with a score according to the criteria described in Table 7. Similarly, the movement of the tear fluid lipid layer before the application to eyes was evaluated with a score. Here, a higher score represents that the lipid layer of the tear film became thin or inhomogeneous, thus the tear film became unstable. The difference of the score before and after the application to eyes was considered as an improvement degree of tear fluid stability, and was evaluated according to the criteria described in Table 8. The results of the average score for the three subjects were shown in Table 9.

TABLE 7

| Criteria | Score |
| --- | --- |
| Color is off-white and there is no movement of tear film that can be observed. | 1 point |
| Color is off-white or yellow, and after blinking tear film spreads from lower eyelid to lower pupillary border. There is a slight disorder in color, contrast or movement of tear film. | 2 points |
| Color is off-white or yellow, and after blinking tear film spreads from lower eyelid to lower pupillary border. There is a disorder in color, contrast or movement of tear film. | 3 points |
| Color consists of an area of off-white or yellow and partially an area showing interference color such as red and green. | 4 points |
| Dry spot is emerged. Color consists of a mixture of an area of off-white or yellow and one or more areas showing interference color such as red and green. | 5 points |
| Dry spot is widely spread. Color consists of a mixture of an area of off-white or yellow and one or more areas showing interference color such as red and green. | 6 points |

TABLE 6

| Soft contact lens | Evaluation Item | Evaluation-2 for area of dry spot | | | | | | | |
| --- | --- | --- | --- | --- | --- | --- | --- | --- | --- |
| | | Ex. 1 | Comp. 1 | Comp. 2 | Comp. 3 | Ex. 2 | Ex. 3 | Ex. 4 | Ex. 5 |
| SCL1 | area ratio | 5.7 | 95.0 | 38.3 | 50.0 | 10.0 | 12.3 | 17.7 | 22.3 |
| | relative value | 1.0 | 16.7 | 6.7 | 8.8 | 1.8 | 2.2 | 3.1 | 3.9 |
| SCL2 | area ratio | 3.3 | 84.0 | 93.3 | 96.7 | 5.0 | 6.7 | 26.7 | 28.3 |
| | relative value | 1.0 | 25.5 | 28.3 | 29.3 | 1.5 | 2.0 | 8.1 | 8.6 |

As aforementioned, when the size of dry spot is large, it can be said that eye is under more dryness condition. The result of this test showed that even after a sufficient time passed from the application to eyes, the area ratios of dry spot for the formulations of Examples are small, which means that the tear film on the surface of contact lens is stabilized and that dryness of eye is suppressed remarkably. Also, this result shows an improvement in a symptom of dry eye.

(3) Evaluation of Stability of Tear Fluid

The wetting solution—eye drops for contact lenses was subjected to the usage as a contact lens wetting solution under the condition as described above, and then, the solution was applied to eyes while wearing contact lenses, followed by the evaluation of the stability of the tear fluid under the following condition.

The movement of the tear fluid lipid layer between the beginning of blinking at about 3 minutes after the application to eyes and the next blinking was observed on the dry eye

TABLE 8

| Criteria | An improvement degree of tear fluid stability |
| --- | --- |
| No change or worse compared to the score before the application to eyes | not good |
| Improvement by 1 point compared to the score before the application to eyes | moderate |
| Improvement by 2 points compared to the score before the application to eyes | good |
| Improvement by 3 points and more compared to the score before the application to eyes | very good |

TABLE 9

| Soft contact lens | Improvement degree of tear fluid stability | | | | | | | |
|---|---|---|---|---|---|---|---|---|
| | Ex. 1 | Comp. 1 | Comp. 2 | Comp. 3 | Ex. 2 | Ex. 3 | Ex. 4 | Ex. 5 |
| SCL1 | very good | not good | good | moderate | very good | good | good | good |
| SCL2 | good | not good | not good | moderate | very good | very good | very good | good |

According to the results of the above tests, it was found that for the formulations of Examples, the lipid layer of the tear film was hardly disordered and thus remained stable, while for the formulations of Comparative Examples, the lipid layer of the tear film easily got disordered and became unstable. As aforementioned, it is known that as the lipid layer of tear film becomes thinner, evaporation of tear fluid is promoted and the eye has a tendency to get dried. Thus the above results show that desiccation of eye was suppressed remarkably for the formulations of Examples compared to the formulations of Comparative Examples. Also, this result shows an improvement of a symptom of dry eye.

Test 2: Evaluation of the Sensation in Using the Solution

Ten subjects were evaluated for the following criteria.

After wetting both sides of a contact lens with each one drop of the wetting solution—eye drops, and then the contact lens was fitted. The same wetting solution—eye drops was applied at two minutes after wearing, and sensations in using including a sensation of adstriction (harsh sensation) and a sensation of dryness were scored according to the criteria described in Table 10 and 11 respectively. The average scores of the subjects were evaluated based on the criteria described in Table 12, then the result was shown in Table 13.

TABLE 10

| Criteria | Score |
|---|---|
| Unpleasant sensation of astriction | 1 point |
| Rather unpleasant sensation of astriction | 2 points |
| Little sensation of astriction | 3 points |
| No sensation of astriction | 4 points |

TABLE 11

| Criteria | Score |
|---|---|
| High sensation of dryness | 1 point |
| Moderate sensation of dryness | 2 points |
| Slight sensation of dryness | 3 points |
| No sensation of dryness | 4 points |

TABLE 12

| Criteria | Evaluation |
|---|---|
| 1 point | not good |
| More than 1 point and not more than 2 points | moderate |
| More than 2 points and not more than 3 points | good |
| More than 3 points and not more than 4 points | very good |

TABLE 13

| Criteria: evaluation for sensation in using | Sensation of astriction/Sensation of dryness | | | | | | | |
|---|---|---|---|---|---|---|---|---|
| | Ex. 1 | Comp. 1 | Comp. 2 | Comp. 3 | Ex. 2 | Ex. 3 | Ex. 4 | Ex. 5 |
| Sensation of astriction (SCL1) | good | not good | moderate | moderate | very good | very good | good | good |
| Sensation of astriction (SCL2) | very good | moderate | good | good | very good | good | good | very good |
| Sensation of dryness (SCL1) | very good | not good | moderate | not good | very good | very good | good | very good |
| Sensation of dryness (SCL2) | very good | not good | moderate | not good | very good | good | very good | very good |

According to the above test results, for the formulations of Examples, a sensation of adstriction (harsh sensation) and a sensation of dryness as subjective symptoms were suppressed remarkably.

Test 3: Corroborative Analysis on Usefulness in a Combination of the Formulations Eye drops, contact lens wetting solutions or wetting solution—eye drops for contact lenses of the formulation 1, 2 and 3 respectively was prepared by the formulations of Table 14 according to a usual preparative method (conventional method) of eye drops and the like, and were filled in polyethylene terephthalate containers (volume 10 mL) and were plugged with nozzles and caps. Unless stated otherwise, the test methods were similar to the above Test 1 and Test 2 and then the corroborative analyses on usefulness in a combination of the formulations were conducted. The result is shown in Table 15. Here, the formulation 1 and the formulation 3 are the formulations of the ophthalmic compositions of the present invention, and specifically, the same formulation was used for the formulation 1 and Example 1 in Table 1, and also for the formulation 3 and Example 3 in Table 1 respectively. Also, the same formulation was used for the formulation 2 and Comparative Example 4 in Table 1.

TABLE 14

| | Form. 1 | Form. 2 | Form. 3 |
|---|---|---|---|
| HPMC[1) | 0.2 | — | — |
| polyvinyl pyrrolidone K90 | — | — | 2.5 |
| sodium chondroitin sulfate | 0.5 | — | 0.3 |
| sodium chloride | 0.44 | 0.44 | 0.44 |
| potassium chloride | 0.08 | 0.08 | 0.08 |
| polysorbate 80 | 0.05 | — | 0.05 |
| boric acid | 1.0 | 1.0 | 1.0 |

TABLE 14-continued

|   | Form. 1 | Form. 2 | Form. 3 |
|---|---|---|---|
| borax | 0.2 | 0.2 | 0.2 |
| edetate sodium | 0.05 | 0.05 | 0.05 |
| purified water | q.s. | q.s. | q.s. |
| total volume | 100 mL | 100 mL | 100 mL |
| pH | 7.3 | 7.3 | 7.3 |
| osmolality ratio | 1.2 | 1.2 | 1.2 |

[1])Hydroxypropyl methylcellulose 2906 (trade name: 65SH-4000, Shin-Etsu Chemical. Co., Ltd.)

TABLE 15

|  |  | Ex. 1 | | Comp. 1 | | Comp. 2 | | Comp. 3 | |
|---|---|---|---|---|---|---|---|---|---|
|  |  | Timing of application | | | | | | | |
|  |  | Fitting | Application to eyes | Fitting | Application to eyes | Fitting | Application to eyes | Fitting | Application to eyes |
|  |  | | | | Formulation | | | | |
|  |  | 1 | 1 | 1 | 2 | 2 | 1 | 2 | 2 |
|  |  | | | | Dosage form[1]) | | | | |
|  |  | Wetting solution - eye drops | Wetting solution - eye drops | Wetting solution | Eye drops | Wetting solution | Eye drops | Wetting solution - eye drops | Wetting solution - eye drops |
| Evaluation of the area of dry spot-1 Analysis B (SCL1) | | 1 | | 13.6 | | 6.4 | | 16.1 | |
| Evaluation of the area of dry spot-1 Analysis B (SCL2) | | 1 | | 18.0 | | 19.0 | | 44.6 | |
| Evaluation of the area of dry spot-2 (SCL1) | Area ratio | 7.7 | | 78.3 | | 71.7 | | 91.3 | |
| | Relative value | 1 | | 10.2 | | 9.3 | | 11.9 | |
| Evaluation of the area of dry spot-2 (SCL2) | Area ratio | 5.0 | | 86.7 | | 78.3 | | 98.3 | |
| | Relative value | 1 | | 17.3 | | 15.7 | | 19.7 | |
| Improvement of stability of tear fluid (SCL1) | | Very good | | Not good | | Moderate | | not good | |
| Improvement of stability of tear fluid (SCL2) | | Good | | Not good | | Moderate | | not good | |
| Sensation of astriction (SCL1) | | Good | | Moderate | | Moderate | | not good | |
| Sensation of astriction (SCL2) | | Very good | | Moderate | | Good | | not good | |
| Sensation of dryness (SCL1) | | Very good | | Not good | | Not good | | not good | |
| Sensation of dryness (SCL2) | | Very good | | moderate | | not good | | not good | |

|  | Ex. 2 | | Comp. 4 | | Comp. 5 | |
|---|---|---|---|---|---|---|
|  | Timing of application | | | | | |
|  | Fitting | Application to eyes | Fitting | Application to eyes | Fitting | Application to eyes |
|  | | | | Formulation | | |
|  | 3 | 3 | 3 | 1 | 1 | 3 |
|  | | | Dosage form[1]) | | | |
|  | Wetting solution - eye drops | Wetting solution - eye drops | Wetting solution | Eye drops | Wetting solution | Eye drops |
| Evaluation of the area of dry spot-1 Analysis B (SCL1) | 3.7 | | 6.7 | | 13.4 | |
| Evaluation of the area of dry spot-1 Analysis B (SCL2) | 2.6 | | 14.8 | | 19.0 | |

TABLE 15-continued

| | | | | |
|---|---|---|---|---|
| Evaluation of the area of dry spot-2 (SCL1) | Area ratio | 25.0 | 46.7 | 77.7 |
| | Relative value | 3.2 | 6.1 | 10.1 |
| Evaluation of the area of dry spot-2 (SCL2) | Area ratio | 7.7 | 58.3 | 60.3 |
| | Relative value | 1.5 | 11.7 | 12.1 |
| Improvement of stability of tear fluid (SCL1) | | Good | Good | Moderate |
| Improvement of stability of tear fluid (SCL2) | | Very good | Moderate | Moderate |
| Sensation of astriction (SCL1) | | Very good | Moderate | Good |
| Sensation of astriction (SCL2) | | Good | Moderate | Moderate |
| Sensation of dryness (SCL1) | | Very good | Moderate | Good |
| Sensation of dryness (SCL2) | | Good | Not good | Moderate |

1) Terms: "Wetting solution" and "Wetting solution - eye drops" represent "Contact lens wetting solution" and "Wetting solution - eye drops for contact lenses", respectively.

When the cases of using the formulation of the present invention as a wetting solution—eye drops for contact lenses (Practical Test Examples 1 and 2) are compared with the case of using the different formulation from that of the present invention as a wetting solution—eye drops for contact lenses (Comparative Test Example 3), Practical Test Examples 1 and 2 showed higher stability of the tear fluid lipid layer and remarkably smaller score in the evaluation for the area of dry spot, resulting in giving remarkably higher suppression of dryness of eyes. Additionally, an advantageous effect was found on a sensation of adstriction and a sensation of dryness as subjective symptoms. Furthermore, even though the formulations used were within the scope of the composition of the present invention, the case in which the same composition was used as the wetting solution—eye drops for contact lenses to the same contact lens or the eyeball at the time of fitting and application to eyes (Practical Test Examples 1 and 2) was compared with the case in which different compositions were used at the time of fitting and applying to eyes (Comparative Test Examples 4 and 5), Practical Test Examples 1 and 2 showed remarkably advantageous effect.

Test 4: Evaluation of the Improvement Effect on Eye Strain
(Test Method)

The improvement effect on eye strain was evaluated with the wetting solution—eye drops for contact lenses of the formulation 1 in Table 14 (which was the same as Example 1). Flicker fusion threshold was used as an index of the evaluation.

Specifically, four subjects who had worn contact lenses for five days and more in a week and were susceptible to eye strain wore contact lenses for eight hours and more in a day, and thereafter flicker fusion threshold in a condition of wearing contact lenses (flicker fusion threshold before dosing) were measured. The contact lens used by the subjects were (1) soft contact lens Group IV Johnson & Johnson K. K., main material: Senofilcon A (silicone-hydrogel material); (2) soft contact lens Group IV Johnson & Johnson K. K., main material: Etafilcon A; (3) soft contact lens Group IV Cooper Vision K. K. and (4) oxygen permeable hard contact lens.

Then after a sufficient time has passed, the contact lenses were once removed from both eyes, and each one drop of the wetting solution—eye drops for contact lenses of the formulation 1 was added dropwise directly into the concave face (the inside face, which contacts with cornea) of the contact lens, the contact lenses were fitted again to both eyes, and after fifteen minutes, each one drop of the wetting solution—eye drops for contact lenses of the formulation 1 was applied to both eyes, and thereafter flicker fusion threshold (flicker fusion threshold after dosing) was measured (Practical Test Example 3).

On the other day, the flicker fusion threshold before dosing was measured in a similar manner and the eye drops of the formulation 1 was applied in one drop each to both eyes while wearing contact lenses, and after 15 minutes, eye drops for contact lenses of the formulation 1 was applied in one drop each to both eyes again and then flicker fusion threshold (flicker fusion threshold after dosing) was measured (Comparative Test Example 6). An improvement rate of flicker fusion threshold was calculated using the obtained flicker fusion threshold according to the equation 1 given below.

The flicker fusion threshold represents critical frequency at which a flickering light appears to be steady to the eye as the flickering frequency of the light is gradually increased. Flicker value can be used as an index to determine eye strain or loss of sensory function. In other words, an improvement of the flicker fusion threshold is an index of an improvement of eye strain (in particular, eye strain caused by physical or mental fatigue accompanied by loss of sensory function) or asthenopia.

In this test, the flicker fusion threshold was measured with an instrument and a condition as described below.

Instrument: Roken digital flicker RDF-1 (Shibata Scientific Technology Ltd.);

Illuminance: The illuminance was set to the value that can be easily observed by a measurer;

Distance: The distance was set to the position that can be easily observed by a measurer (a position at which "K" character can be seen most clearly by a measurer);

SCAN knob (initial flicker frequency to be descended): 60 Hz;

MANU-AUTO: Set to AUTO.

The obtained flicker fusion threshold was used for calculating the value of the improvement of eye strain (an improvement rate of flicker fusion threshold) according to the following equation 1:

Improvement rate of flicker fusion threshold (%)=
(Flicker fusion threshold after dosing (Hz)−
Flicker fusion threshold before dosing (Hz))/
Flicker fusion threshold before dosing (Hz)×100    [Equation 1]

The average of the results for four subjects is shown in Table 16. According to this result, for all the four subjects a remarkable increase in the improvement rate of flicker fusion threshold was observed in Practical Test Example 3 compared to Comparative Test Example 6. In this field of the art, it is normally thought that whether an effect (clear change) is present or not is judged based on the level of about 3% of the improvement rate of flicker fusion threshold. According to the above results, it was confirmed that the wetting solution—eye drops for contact lenses of the present invention was remarkably superior in an improvement effect on eye strain, asthenopia, or physical or mental fatigue, and thus is very useful as compared to the usage only as eye-drops like a conventional use of eye drops.

TABLE 16

|  | Practical Test Example 3 (fitting + application to eyes) | Comp. Test Example 6 (application to eyes + application to eyes) |
|---|---|---|
| Improvement rate of flicker fusion threshold (%) | 3.4 | 0.2 |

Examples 6 to 10

The wetting solution—eye drops for contact lenses (Examples 6 to 10) were prepared according to the formulations described in Table 17. The unit for each ingredient to be compounded in Table 17 is g/100 mL. All these Examples showed similar effects of the invention as Example 1 in the above Tests 1 to 4.

Test 5: Evaluation of an Improvement Effect on Contrast Sensitivity (Test Method)

An improvement effect on contrast sensitivity was evaluated using the wetting solution—eye drops for contact lenses of Examples 1 to 10 in Table 1 and Table 17.

Specifically, the contrast sensitivity was measured for the eight subjects who had worn contact lens for five days and more a week in a condition of wearing contact lens by using Vision Contrast Test System (VCTS (trademark)) Chart Test (as a blank). A detailed evaluation method was referred to the instruction (VCTS Chart Examination Procedure, Vistech Consultants, Inc.) packaged with the VCTS Chart Test. Also the contrast sensitivity value was calculated by using a table of Contrast Sensitivity Value Key in the said instruction. The scores included five points of A (1.5 cpd (i.e. cycles/deg)), B (3 cpd), C (6 cpd), D (12 cpd) and E (18 cpd).

Firstly, the wetting solution—eye drops for contact lenses of the formulation 1 in Table 14 (which is the same as Example 1) was subjected to the usage as a contact lens wetting solution, and after two minutes, the same solution was applied to eyes while wearing contact lens, then after one minute the contrast sensitivity was measured (Practical Test Example 4). Four subjects wore the contact lenses of the above SCL1, and the other four subjects wore SCL2.

The average of the results obtained from eight subjects is shown in FIG. 1. According to this result, for all the eight subjects, Practical Test Example 4 wherein the formulation 1 was used as the wetting solution—eye drops for contact lenses showed remarkable improvement in contrast sensitivity compared to the blank.

Similarly, for the wetting solution—eye drops for contact lenses prepared according to Examples 2 to 10, the contrast sensitivity in the point of B (3 cpd), at which there was the biggest difference between Examples and the blank, were measured and the average of the result is shown in Table 18. Ten subjects wore the contact lens of the above SCL1, and the other 10 subjects wore SCL2.

TABLE 17

|  | Ex. 6 | Ex. 7 | Ex. 8 | Ex. 9 | Ex. 10 |
|---|---|---|---|---|---|
| HPMC[1] | — | — | — | 0.2 | 0.2 |
| hydroxyethylcellulose[2] | 0.2 | 0.6 | — | — | — |
| polyvinyl alcohol (partially saponified product) | — | — | — | — | 1.0 |
| dextran 70 | — | — | 0.1 | — | — |
| macrogol 4000 | — | — | — | 1 | — |
| sodium chondroitin sulfate | — | 0.5 | 0.05 | — | 0.5 |
| alginic acid | 0.05 | — | — | 0.1 | — |
| polysorbate 80 | 0.1 | — | — | — | 0.3 |
| POE hydrogenated castor oil 60 | — | 0.05 | 0.05 | 0.3 | — |
| poloxamer 407 | — | — | — | — | 0.1 |
| sodium chloride | 0.44 | 0.22 | 0.44 | 0.44 | 0.44 |
| potassium chloride | 0.08 | 0.08 | 0.08 | 0.08 | 0.08 |
| boric acid | 1 | 1 | 1 | 1 | — |
| borax | 0.2 | 0.2 | 0.2 | 0.2 | — |
| sodium dihydrogen phosphate | — | — | — | — | 0.25 |
| disodium hydrogen phosphate | — | — | — | — | 0.05 |
| edetate sodium | 0.05 | 0.05 | 0.05 | 0.05 | 0.05 |
| polyhexanide hydrochloride | — | — | — | — | 0.0001 |
| purified water | q.s. | q.s. | q.s. | q.s. | q.s. |
| total volume | 100 mL | 100 mL | 100 mL | 100 mL | 100 mL |
| pH | 7.3 | 7.3 | 7.3 | 7.3 | 6.5 |
| osmolality ratio | 1.2 | 1.0 | 1.2 | 1.2 | 0.7 |
| viscosity (mPa·s) | 4.3 | 60 | 1.2 | 5 | 6 |

[1]Hydroxypropyl methylcellulose (trade name: 65SH-4000 (Shin-Etsu Chemical. Co., Ltd.)
[2]Trade name: CF-V Sumitomo Seika Chemicals Co., Ltd.

TABLE 18

|  |  | Blank | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|---|
| contrast sensitivity | SCL1 | 34 | 65 | 50 | 49 | 49 | 50 | 58 | 60 | 46 | 61 | 48 |
|  | SCL2 | 29 | 65 | 51 | 65 | 44 | 44 | 58 | 58 | 44 | 60 | 44 |

As is evident from the above result, the use of the wetting solution—eye drops for contact lenses of Examples 2 to 10 also exhibited remarkable improvement in contrast sensitivity compared to the blank, in the same manner as Example 1.

Formulation Example 1 to 10

The wetting solution—eye drops for contact lenses (Formulation Example 1 to 10) were prepared according to the prescriptions described in Table 19. The unit for each ingredient to be compounded in Table 19 is g/100 mL.

TABLE 19-1

|  | Form. 1 | Form. 2 | Form. 3 | Form. 4 | Form. 5 |
|---|---|---|---|---|---|
| HPMC[1] | 0.01 | 0.2 | — | — | — |
| hydroxyethylcellulose[2] | — | — | 0.05 | 0.4 | 0.01 |
| polyvinyl alcohol (partially saponified product) | — | — | 2 | — | — |
| polyvinylpyrrolidoneK90 | 2.5 | — | — | 1.5 | — |
| carboxy vinyl polymer | — | 0.2 | — | — | 0.2 |
| sodium chondroitin sulfate | 0.001 | 0.01 | — | — | 0.8 |
| alginic acid | — | — | 0.1 | 0.01 | — |
| polysorbate 80 | 0.05 | — | — | — | 0.1 |
| POE hydrogenated castor oil 60 | 0.05 | 0.5 | 0.1 | 0.2 | — |
| potassium magnesium aspartate | — | 1 | — | — | — |
| epsilon-aminocaproic acid | — | — | — | 2 | — |
| sodium chloride | 0.44 | 0.22 | 0.44 | 0.44 | 0.3 |
| potassium chloride | 0.08 | 0.08 | 0.08 | 0.08 | 0.08 |
| boric acid | 1 | 1 | — | 1.8 | 1 |
| borax | 0.2 | 0.2 | — | 0.2 | 0.2 |
| disodium hydrogen phosphate•12 hydrates | — | — | 0.3 | — | — |
| sodium dihydrogen phosphate•2 hydrates | — | — | 0.02 | — | — |
| edetate sodium | 0.05 | 0.05 | 0.05 | 0.01 | 0.2 |
| polyhexanide hydrochloride | — | 0.0001 | — | — | — |
| potassium sorbate | — | — | 0.1 | — | — |
| purified water | q.s. | q.s. | q.s. | q.s. | q.s. |
| total volume | 100 mL | 100 mL | 100 mL | 100 mL | 100 mL |
| pH | 7.3 | 7.3 | 6.5 | 7.3 | 7.3 |
| osmolality ratio | 1.2 | 1.0 | 1.3 | 1.6 | 1.1 |
| viscosity (mPa·s) | 2.0 | 15 | 4.0 | 20 | 15 |

[1]Hydroxypropyl methylcellulose (trade name: 65SH-4000 (Shin-Etsu Chemical. Co., Ltd.)
[2]Trade name: CF-V Sumitomo Seika Chemicals Co., Ltd.

TABLE 19-2

|  | Form. 6 | Form. 7 | Form. 8 | Form. 9 | Form. 10 |
|---|---|---|---|---|---|
| HPMC[1] | — | — | — | — | 0.1 |
| hydroxyethylcellulose[2] | — | — | — | — | 0.1 |
| carboxymethylcellulose sodium[3] | 0.4 | — | — | — | 0.4 |
| methylcellulose[4] | — | 0.4 | — | — | — |
| polyvinyl alcohol (partially saponified product) | — | — | 1.2 | — | — |
| polyvinylpyrrolidoneK90 | — | — | — | 2 | 1 |
| dextran 70 | 0.1 | — | — | — | — |
| macrogol 4000 | — | 1 | — | — | — |
| sodium chondroitin sulfate | — | — | 0.01 | 0.1 | 0.05 |
| alginic acid | 0.2 | 0.05 | — | — | 0.05 |
| polysorbate 80 | — | 0.005 | 0.5 | — | 0.05 |
| POE hydrogenated castor oil 60 | 0.005 | — | — | 0.05 | — |
| poloxamer 407 | — | — | — | 0.05 | 0.1 |
| potassium aspartate | — | — | 1 | 1 | — |
| potassium magnesium aspartate | — | 0.2 | — | — | — |

TABLE 19-2-continued

|  | Form. 6 | Form. 7 | Form. 8 | Form. 9 | Form. 10 |
|---|---|---|---|---|---|
| aminoethylsulfonic acid | 1 | — | — | — | 1 |
| pyridoxine hydrochloride | — | — | 0.1 | — | — |
| sodium hyaluronate | — | — | — | 0.005 | 0.001 |
| sodium chloride | 0.44 | 0.44 | 0.44 | 0.44 | 0.44 |
| potassium chloride | 0.08 | 0.08 | 0.08 | 0.08 | 0.08 |
| sodium hydrogen carbonate | — | — | — | 0.4 | — |
| calcium chloride | — | — | — | 0.005 | — |
| boric acid | 1 | 1 | — | 1 | 1 |
| borax | 0.2 | 0.2 | — | 0.2 | 0.2 |
| disodium hydrogen phosphate•12 hydrates | — | — | 0.3 | — | — |
| sodium dihydrogen phosphate•2 hydrates | — | — | 0.02 | — | — |
| edetate sodium | 0.05 | 0.05 | 0.05 | 0.05 | 0.05 |
| polyhexanide hydrochloride | — | 0.00005 | — | — | — |
| potassium sorbate | — | 0.1 | — | — | — |
| purified water | q.s. | q.s. | q.s. | q.s. | q.s. |
| total volume | 100 mL | 100 mL | 100 mL | 100 mL | 100 mL |
| pH | 7.3 | 7.3 | 6.5 | 7.3 | 7.3 |
| osmolality ratio | 1.5 | 1.2 | 1.3 | 1.5 | 1.5 |
| viscosity (mPa · s) | 12 | 15 | 2.5 | 5 | 18 |

[1] Hydroxypropyl methylcellulose (trade name: 65SH-4000 (Shin-Etsu Chemical. Co., Ltd.)
[2] Trade name: CF-V Sumitomo Seika Chemicals Co., Ltd.
[3] Trade name: AG Gum M Dai-ichi Kogyo Seiyaku Co., Ltd.
[4] Trade name: SM8000 Shin-Etsu Chemical. Co., Ltd.

INDUSTRIAL APPLICABILITY

The ophthalmic composition of the present invention can stabilize the tear film during wearing contact lens, suppress eye dryness, impart a favorable sensation in using, is highly convenient with no risk of misuse and shows a high efficiency in the course from manufacturing to sales, which therefore are very useful in the industry.

The invention claimed is:

1. A method of suppressing eye desiccation or dry eye and alleviating eye strain with an ophthalmic composition, said method comprising:
    first, selecting (A) one or more member(s) selected from the group consisting of hydroxyethyl cellulose, hydroxypropylmethyl cellulose, polyvinyl pyrrolidone, polyethylene glycol, dextran, and salts thereof; (B) one or more member(s) selected from the group consisting of chondroitin sulfate, alginic acid, and salts thereof; and (C) one or more member(s) selected from the group consisting of polyoxyethylene sorbitan fatty acid ester and polyoxyethylene hydrogenated castor oil to provide a specific ophthalmic composition, then
    (i) adding said specific ophthalmic composition directly to a contact lens dropwise in order to wet said contact lens before fitting said contact lens;
    (ii) fitting said contact lens to an eye; and
    (iii) wetting said contact lens by applying to said eye during wearing of said contact lens an ophthalmic composition which has the same chemical composition as the specific ophthalmic composition added to said contact lens, thereby suppressing dry eye in said eye, suppressing desiccation of said eye, or alleviating strain in said eye.

2. The method according to claim 1, wherein the ophthalmic composition comprises component (A) in an amount of 0.0001 to 25 (w/v) %, component (B) in an amount of 0.0005 to 10 (w/v) %, and component (C) in an amount of 0.001 to 5 (w/v) %.

3. A method of handling a contact lens comprising the following steps:
    first, selecting (A) one or more member(s) selected from the group consisting of hydroxyethyl cellulose, hydroxypropylmethyl cellulose, polyvinyl pyrrolidone, polyethylene glycol, dextran, and salts thereof; (B) one or more member(s) selected from the group consisting of chondroitin sulfate, alginic acid, and salts thereof; and (C) one or more member(s) selected from the group consisting of polyoxyethylene sorbitan fatty acid ester and polyoxyethylene hydrogenated castor oil to provide a specific ophthalmic composition, then
    (1) adding said specific ophthalmic composition dropwise directly to a contact lens in order to wet the contact lens before fitting the contact lens;
    (2) fitting the wetted contact lens to an eye; and
    (3) wetting the fitted contact lens by applying an ophthalmic composition which has the same chemical composition as the specific ophthalmic composition added to said contact lens to said eye during wearing of the contact lens.

4. The method according to claim 3, wherein the ophthalmic composition comprises component (A) in an amount of 0.0001 to 25 (w/v) %, component (B) in an amount of 0.0005 to 10 (w/v) %, and component (C) in an amount of 0.001 to 5 (w/v) %.

* * * * *